United States Patent [19]

Larsson et al.

[11] Patent Number: 5,451,372
[45] Date of Patent: Sep. 19, 1995

[54] DEVICE FOR MONITORING STERILIZATION PROCESS UTILIZING 100% ETHYLENE OXIDE

[75] Inventors: Raymond P. Larsson, Denville; Judith Nieves, Newark, both of N.J.

[73] Assignee: Pymah Corporation, Flemington, N.J.

[21] Appl. No.: 109,667

[22] Filed: Aug. 20, 1993

[51] Int. Cl.6 .................................................. G01N 31/22
[52] U.S. Cl. ........................................ 422/58; 422/56; 422/61; 431/1; 431/128
[58] Field of Search ................ 422/56, 58, 61; 436/128.1

[56] References Cited

U.S. PATENT DOCUMENTS 4,138,216  2/1979  Larsson et al. ..................... 422/56

Primary Examiner—Lyle A. Alexander

[57] ABSTRACT

A device is disclosed for monitoring an ethylene oxide sterilization process in which 100% ethylene oxide is utilized as the sterilant comprising a wick impregnated with an ethylene oxide responsive chemical compound, a quantifier and a pH sensitive dye; an ethylene oxide impervious backing strip upon which the wick is mounted; and a cover strip having an ethylene oxide impervious film. The backing and cover strip are adhered to one another, and in intimate contact with and sealed to the wick. At least one of the cover strip and backing strip having a centrally located perforation through which the ethylene oxide sterilant can access the wick.

19 Claims, 1 Drawing Sheet

DEVICE FOR MONITORING STERILIZATION PROCESS UTILIZING 100% ETHYLENE OXIDE

BACKGROUND OF THE INVENTION

The sterilization of surgical supplies and parenteral drugs is a carefully controlled process. An effective commonly used method of sterilization is by steam under pressure. However, many surgical instruments and supplies are adversely affected by heat. Sterilization at high temperatures is not practical for such items.

An outgrowth of agricultural and industrial fumigation is sterilization utilizing gaseous ethylene oxide. The advantages of sterilization utilizing ethylene oxide include, sterilization at lower temperatures thereby avoiding the detrimental effect of elevated temperatures on the goods to be sterilized, items to be sterilized can be terminally sterilized in their packages, and the equipment required to carry out the process is simple.

The preferred method of utilizing ethylene oxide in sterilization process has been to dilute the ethylene oxide with a gas inert to the ethylene oxide, such as Freon ®, a fluoro-chloro substituted ethane or $CO_2$. The Freon ® selected should be a gas at the sterilization temperature. Generally, the concentration of ethylene oxide is about 450 mg/lt to about 1,500 mg./lt, while processing temperatures can range from about 70° to about 140° F. Preferably, where the diluent is Freon ®, the ethylene oxide concentration is about 12 wt. %. in the sterilant gas. Where the diluent is $CO_2$, the concentration of ethylene oxide is about 10 wt. %. For such processes, the parameters which affect ethylene oxide sterilization processes are exposure time, gas concentration, temperature and humidity. For diluted ethylene oxide, relative humidities below 30% RH limit the effectiveness of the ethylene oxide sterilization process. High humidities, e.g., above 90% RH, also results in inadequate processing.

The classical method for determining whether or not a particular sterilization process has been effective is to include in the system exposed to the sterilizing process a suitable resistant organism. For ethylene oxide sterilization the organism of choice is spores of *Bacillus subtilis var. niger,* since these spores exhibit high resistance to ethylene oxide. Such a control method suffers from the fact that at least several days are required to culture the spores in order to confirm the effectiveness of the sterilization process. Additionally, the spores being living organisms, the rate at which they are killed is a logarithmic relationship with time, resulting in a broad time window between initial and complete spore kill.

In the field of sterilization by heat various physical indicators have been developed to monitor the sterilization process. These devices vary in quality from the simplest melt indicators which show whether or not a particular temperature has been achieved to more sophisticated devices such as PymaH Corporations Thermalog ® S, which integrates the time, temperature and steam exposure parameters of the sterilization process. Similarly, various physical indicators have been developed for monitoring the ethylene oxide sterilization process.

An indicator comprising 4(4-nitrobenzyl)pyridine applied to a paper strip has been used in ethylene oxide sterilization process monitoring; see for example *Journal of Pharmaceutical Sciences,* Brewer et al., pages 57-59, January 1966. Other compounds, including pyridines and quinolines have also been utilized; see U.S. Pat. No. 3,627,469. An ink composition has been prepared as a telltale for ethylene oxide sterilization which utilizes the fact that $MgCl_2$ reacts with ethylene oxide to produce a base, $Mg(OH)_2$, which is detected by a pH sensitive dye; see U.S. Pat. No. 3,098,751. This same chemical reaction has been used to prepare a physical sterilization indicator by depositing reactants on an absorbent material and enclosing the composition in a sealed envelope of gas permeable film such as polyethylene; see Royce and Bower "An Indicator Control Device for ethylene Oxide Sterilization." *J. Pharm. and Pharm.* 111 Suppl. 294T-298T.

A more recent development in the area of ethylene oxide monitoring is disclosed in U.S. Pat. No. 4,138,216. The device disclosed comprises a wick impregnated with $MgCl_2$ and a pH sensitive dye is enclosed in a gas impervious envelop having one end open. An additional constituent is an acidic material, e.g., tartaric acid, which acts as a quantifier to adjust the time response of the device. This latter device is particularly useful in ethylene oxide sterilization monitoring because it is responsive to humidity levels as well as temperature and gas concentration.

As a result of the environmental problems attendant to discarding the spent ethylene oxide sterilant gas mixture, there has been a trend toward using 100% ethylene oxide in the sterilization process. The primary advantage is that the sterilant gas can be recycled. In contrast, in order to recycle the diluted ethylene oxide sterilant which is prevalent in the field, the concentration of ethylene oxide must be determined and appropriate amount of the gas added to the sterilant stream in order to bring it to specification. These added steps mitigate against recycling the diluted gas. Unfortunately, the prior art devices do not offer the performance desired when the sterilant gas comprises 100% ethylene oxide.

SUMMARY OF THE INVENTION

It has surprisingly been found that a combination of $MgCl_2$, an acidic quantifier and a pH sensitive dye can be utilized to construct a sterilization monitor useful in ethylene oxide sterilization by adjusting the concentration of constituents and the form of the enclosure utilized for a substrate impregnated with an indicated solution. The enclosure comprises a backing impervious to ethylene oxide and a transparent cover of a material which is impervious to ethylene oxide. The transparent cover is perforated with a centrally located hole to permit entry of the ethylene oxide. The cover can be overlayed with a printed label showing a scale for acceptance or rejection of the process being monitored.

DETAILED DESCRIPTION

Figure 1:
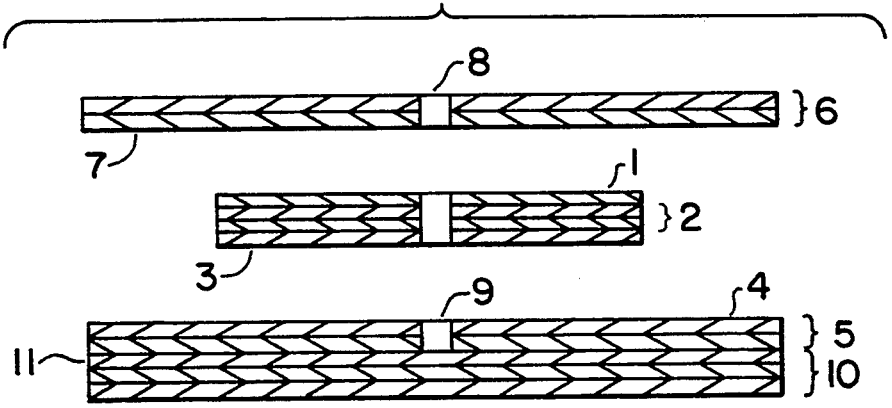
FIG. 1 is an exploded view of the device of this invention.

This invention relates to a physical process monitor for measuring the effectiveness of an ethylene oxide ("ETO") sterilization processes. More particularly it relates a process monitor suitable for use in sterilization processes which utilize 100% ETO.

The process monitor of this invention comprises a wick of absorbent material completely enclosed in an ETO impervious pouch having a single centrally located opening. The wick is impregnated with a chemical compound which will react with ETO to produce a basic reaction product, the presence of which is detected by a pH indicator incorporated into the wick. To control the time response of the process monitor a quantifier is incorporated into the wick. the quantifier is an acidic material which preferentially reacts with the basic reaction product, thereby preventing a color change of the pH indicator. The color change produced by the pH indicator reaction with the basic material moves along the wick outwardly in all directions from the centrally located opening.

Illustrative non-limiting examples of chemical compounds which react with ETO to produce a basic reaction product are $MgCl_2$, $FeCl_2$, $ZnCl_2$ and hydrates of these salts. A particularly preferred compound is the hydrate of magnesium chloride ($MgCl_2.6H_2O$). As used in the specification and claims the term "ethylene oxide responsive chemical compound" means a chemical compound which will react with ETO to produce a basic reaction product, of which the foregoing compounds are illustrative.

The material used for the wick is not critical. It need only be sufficiently absorbent to take up a solution containing the chemical compound, and be substantially unreactive to ETO or the basic reaction product at the concentrations it exists in the process monitor. Illustrative non-limiting examples of suitable absorbent material useful as wicks in the practice of this invention are paper and fabrics such as polyamide, polyester, cotton etc. whether woven or non-woven. Paper is the preferred wick material. These material will general imbibe about one ml. of water solution per gram of material.

Illustrative, non-limiting examples of pH sensitive dyes suitable for use in the practice of this invention are bromphenol blue, thymol blue and xylenol blue. The pH sensitive dye preferably has at least one $pK_a$ value which is less than 8, more preferably less than 7. The preferred pH sensitive dye is bromphenol blue. The term "pH sensitive dye" as used in the specification and claims means a pH indicator which has at least one $pK_a$ value of less than 8.

The quantifier material is a compound which reacts preferentially with the basic reaction product, thereby neutralizing it and preventing a color change in the pH sensitive dye. The preferred quantifiers are organic acids and acid salts. Illustrative non-limiting examples of quantifiers are tartaric acid, oxalic acid, citric acid, sodium bisulfate, etc. The term "quantifier" as used in the specification and claims means an acidic compound which has a $pK_a$ value of less than 6, and which reacts with the base produced by the reaction of ETO with the ethylene oxide responsive chemical compound, and is thereby neutralized.

Any material which is impervious to ETO may be used as the envelope to contain the wick means onto which the ethylene oxide responsive chemical compound has been deposited. Of course at least a part of the envelop material must be transparent to permit observation of the color change of the wick means. The preferred envelop materials are polymeric films. However, metal foils such as aluminum foil, or aluminum foil coated with polyethylene are also useful for at least a part of the envelop. Illustrative, non-limiting examples of polymeric films useful as envelop materials are trifluoropolyethylene, polycarbonates, polyvinylidene chlorides or polyesters, in particular esters of ethylene glycol and terephthalic acid, e.g., Mylar ®.

In preparing the wick means, the wick composition is impregnated with a solution containing the ethylene oxide responsive chemical compound, the quantifier and the pH sensitive dye in a suitable solvent. Preferably the solvent is a volatile material such as water or $C_1-C_4$ alcohols. Where alcohol is used as the solvent, it is necessary to make up fresh solution daily since magnesium salts catalyze the formation of esters of the alcohol and the quantifier. Alcohols are, therefore, preferably utilized in combination with water, which suppresses the esterification reaction. The alcohol when used comprises about 40 to about 70 wt. % of the solvent. From both the standpoint of safety and economics the preferred solvent is water.

The term "solvent" as used in the specification and claims means a normally liquid compound which is a solvent for the chemical components to be applied to the wick means, and which can be readily removed from the wick means by evaporation. The solvent must be inert to the components to be deposited on the wick means during the impregnation and drying steps. Illustrative, non-limiting examples of solvents suitable for use in the practice of this invention are water, methanol, ethanol, methyl acetate, ethyl acetate, propanol, water and mixtures thereof.

In the preparation of the process monitor of this invention the first step is to prepare the wick means. The preferred wick material is paper. Typical papers which can be used are filter paper stock such as Whatman #1 filter paper and Schleicher & Schull ("S&S") 598 paper or S&S 410 paper. These papers are preferred since they are of good quality, free of contaminants which might interfere with the operation of the monitor.

While the absorbent material may be impregnated directly, from a practical operating stand point it is preferred to adhere the absorbent material to a polymeric carrier film backing to give it sufficient strength to be readily handled as a moving web in the wet state. The absorbent material may be bonded to the polymeric film adhesively or by heat sealing. In a preferred embodiment of the invention a laminate of Mylar ® and Surlyn ® 1601 polymers is used both as the carrier film for the absorbent material and as the ETO impervious film for the envelop. Surlyn ® 1601 is believed to be a sodium ionomer of polyethylene grafted with an organic acid, e.g., acrylic acid. The Mylar ® layer is about 0.5 mils thick, while the Surlyn ® layer is about 2 mils thick.

The paper wick means is heat sealed to the Surlyn ® layer and impregnated with the solution containing the chemical compounds of this invention. It is then passed through rollers to remove excess solution, and subsequently dried by passing it over heated rollers. After treatment and drying a section of suitable size for the wick means is punched out of the web.

Referring now to FIG. 1, the wick means comprising the paper, 1, adhered to mylar laminate, 2, is coated with an acrylic adhesive layer, 3. The wick means is then secured to the Surlyn side, 4, of the Mylar laminate, 5 which is to become a surface of the envelope enclosure. A second piece of Mylar substrate, 6, is then brought into juxtaposition with the first Mylar laminate, 5, with the Surlyn surfaces, 4 and 7, in contact with one another. The envelope is then formed by heat sealing the Surlyn ® surface to one another. It will be appreciated that practically the device is formed on a continuous moving web, and each process monitor must then be die punched out of the web.

It will be appreciated by those skilled in the art having access to this disclosure that the envelope may be prepared by adhesive sealing as well as heat sealing. Additionally, graphics containing instructions and a scale may be applied to the process monitor.

In order that the ETO may have access to the wick means a hole is punched through at least one surface of the envelope. Referring a gain to FIG. 1, in one embodiment merely for ease of manufacture a needle of appropriate size is passed through the entire device, leaving holes, 8 and 9, in the upper surface and lower surfaces respectively. While the device is operative with both holes, using the construction described, the lower surface hole, 9, can become plugged with adhesive during the manufacturing process. This occurs in an unpredictable, random manner, and therefore, interferes with the consistent operation of this device. To avoid this inconsistency the lower hole, 9, is sealed.

One method of sealing the hole is to adhere a laminate of paper/aluminum foil/polyethylene/adhesive, 10, to the outer surface of the Mylar laminate by adhesively sealing the polyethylene surface, 11, to the Mylar laminate, 4. A suitable product for this purpose is sold by Tapecon, Inc. The adhesive layer, not shown, is applied to the polyethylene layer, 11.

Initial efforts to prepare a 100% ETO monitor the device of U.S. Pat. No. 4,138,216 was prepared utilizing the Mylar/Surlyn laminate and heat sealing it. The device ran to completion in 30 minutes. This is inadequate since the required sterilization cycle for ETO sterilization is one hour. In an effort to increase the time to completion for the device, several techniques were attempted. The concentration of chemical compounds in the impregnated solution was increased; the quantity of quantifier was increased independent of the amount of $MgCl_2$ utilized; the amount of $MgCl_2$ was increased independent of the amount of quantifier; A higher concentration of chemical compounds was also utilized in conjunction with opening both ends of the device. All of these approaches resulted in failure. Ultimately it was decided that a much larger wick must be used.

A device was prepared using a larger wick means, and all of the above variations were utilized to attempt to obtain a device with an appropriate operating time. Again failure resulted. Attempts were made completely enclosing the wick means and puncturing holes in the envelop to admit ETO. Holes of different sizes were located toward the ends of the device as well as toward the center. Multiple holes were attempted. Ultimately success was achieved with a single centrally located hole. The wick means size used was about one inch by four inches. For this size device the wick was enclosed in an envelope with a sealed land area of about one-quarter inch wide surrounding the wick means. The hole size for this size wick is made with a needle ranging in size from about 0.5 mm to about 0.9 mm.

It will be appreciated that, without undue experimentation, the size of the wick means and hole can be varied while still having a practical, operable device, However it appears that a hole size greater than about 1.6 mm results in a device which runs out of control. In the device of this invention as described the rate controlling factor is the size of the hole. Too small a hole results in a device which runs to slowly for practical operation. While the hole size can be less than 0.5 mm, such a device will be smaller in size, and have limited application. Too large a hole results in a device without any time control capability. The hole size which can be utilized in the practice of this invention is about 0.3 to about 1.6 mm; preferably about 0.4 to about 1.2 mm, e.g., 0.5 to about 1.0 mm. A practical wick size for such a range of hole sizes is about $3 \times \frac{3}{4}$ inches to about $1 \times 4$ inches.

There is some degree of criticality to the concentration of $MgCl_2$ and quantifier which can be used. A typical impregnating solution for the device of the prior art U.S. Pat. No. 4,138,216, comprises 305 grams of magnesium chloride hexahydrate, 150 grams of tartaric acid and 2 grams of bromphenol blue, sodium salt dissolved in five liters of water. In the practice of this invention the impregnating solution can contain the following concentrations of chemical compounds: The ethylene oxide responsive chemical compound can be present at about 95 to about 175 grams per liter, typically about 110 to about 160 grams per liter, e.g. about 120 to about 155 grams per liter. The quantifier can be present at about 47 to about 85 grams per liter, typically about 53 to about 82 grams per liter, e.g., about 58 to about 78 grams per liter. The pH sensitive dye can be present at about 0.6 to about 1.2 grams per liter; typically about 0.7 to about 1.1 grams per liter, e.g., about 0.8 to about 1.0 grams per liter. A typical impregnating solution utilizing magnesium chloride hexahydrate as the ETO responsive chemical compound, tartaric acid as the indicator and bromphenol blue, sodium salt as the pH indicator comprises about 762.5 grams of magnesium chloride hexahydrate, 375 grams of tartaric acid and 5.0 grams of bromphenol blue, sodium salt all dissolved in five liters of water. While the amount of pH indicator utilized is not critical a sufficient amount must be utilized to be effective to ensure ease of readability of the signal obtained.

Figure 2A:
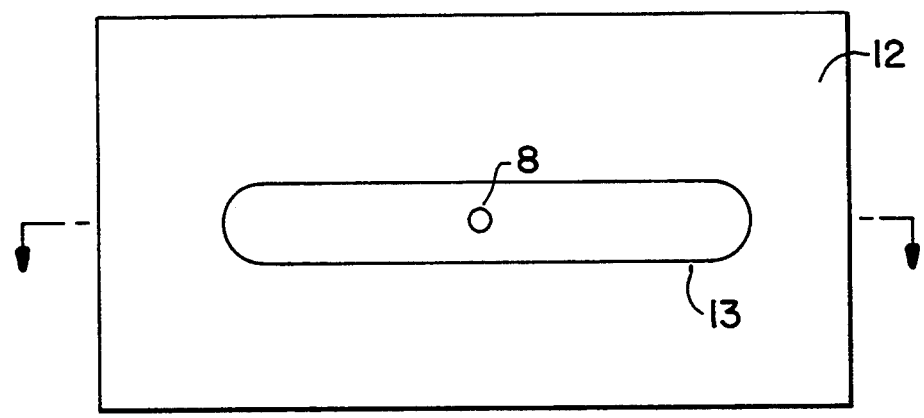
FIGS. 2(a-b) are a plan and elevation view of the device of this invention.
Figure 2B:
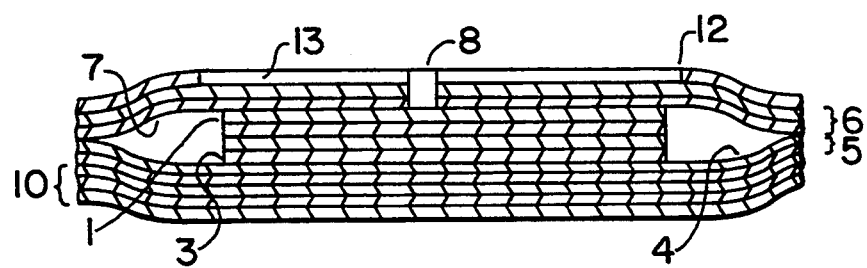

Using the above described magnesium chloride solution, a device was prepared utilizing a wick of S&S 410 paper ($4'' \times 1''$), the above described Mylar/Surlyn laminate as the ethylene oxide impervious film and 3M 467 acrylic adhesive as the adhesive. The device operated in the prescribed manner to monitor a 100% ETO sterilization process. This device is shown in FIG. 2 where the components are as previously described. The completed device also included graphics, 12, having an indication of whether or not sterilization was complete. Only perforation, 8, is shown. It will be appreciated by those skilled in the art having access to this disclosure, that the graphics, 1, can be bonded with a layer of adhesive (not shown) to the upper impervious layer, 6, ad the perforation made through the widow area, 13, and subsequently this composite can heat sealed to the other components of the device. In that way, the perforation appears only in the upper layer, 6, of impervious material.

The device of this invention is sensitive to humidity as well as ETO concentration. Since the sterilization processes to be monitored are intended to use 100% ETO, if the concentration falls below that level, the process monitor will indicate an unsuccessful sterilization process. While the device is sensitive to large variations in temperature, there is only a slight difference in the operation of the device at temperatures about 130° F. to about 140° F., the usual ETO sterilization temperatures.

Unlike the device of U.S. Pat. No. 4,138,216, a critical aspect of the invention is that the cover strip and backing strip must both be in intimate contact with and sealed to the wick means. Unless this condition is met, ETO can move between the wick means and the cover strip or backing strip. In that event the device will not operate properly. The term "wick means" includes both the absorbent material alone and the absorbent material on the carrier film.

What is claimed is:

1. A device for monitoring an ethylene oxide sterilization process in which 100% ethylene oxide is utilized as the sterilant comprising:
   (a) a wick means, said wick means being impregnated with an ethylene oxide responsive chemical compound, a quantifier and a pH sensitive dye;
   (b) an ethylene oxide impervious backing strip upon which the wick means is mounted; and
   (c) a cover strip comprising an ethylene oxide impervious film;
   said backing and cover strip being adhered to one another, and in intimate contact with and sealed to the wicking means; at least one of said cover strip and backing strip having a centrally located perforation of about 0.3 to about 1.6 mm in diameter, through which the ethylene oxide sterilant can access the wick means.

2. The device according to claim 1 wherein the quantifier is tartaric acid, oxalic acid, citric acid or sodium bisulfate.

3. The device according to claim 1 wherein the ethylene oxide responsive chemical compound is $MgCl_2$, $FeCl_2$, $ZnCl_2$ or hydrates thereof.

4. The device according to claim 1 wherein the ethylene oxide responsive chemical compound is $MgCl_2.6H_2O$.

5. The device according to claim 1 wherein the backing strip and cover strip are adhered to one another by heat sealing.

6. The device according to claim 1 wherein the cover strip and backing strip are sealed to the wicking means by heat sealing.

7. The device according to claim 1 wherein the pH sensitive dye has at least one $pK_a$ value of less than 7.

8. The device according to claim 1 wherein the pH sensitive dye is bromphenol blue, thymol blue, xylenol blue or the sodium salt thereof.

9. The device according to claim 1 wherein the backing strip and cover strip comprise a laminate of ethylene glycol-terephthlate polyester and a polyethylene ionomer.

10. The device according to claim 1 wherein
    (a) the ethylene oxide responsive chemical compound is $MgCl_2.6H_2O$;
    (b the quantifier is tartaric acid;
    (c) the wick means comprises a paper strip on a carrier film;
    (d) the pH sensitive dye is bromphenol blue, sodium salt; and
    (e) the ethylene oxide impervious cover strip and backing strip are comprised of a laminate of ethylene glycol-terephthlate polyester and polyethylene ionomer.

11. The device according to claim 10 wherein the cover strip and backing strip are adhered to one another by heat sealing and the cover strip and backing strip are sealed to the wick means by heat sealing.

12. The device according to claim 1 wherein the wick means has been impregnated from a solution comprising about 110 to about 160 grams per liter of ethylene oxide responsive chemical compound, about 53 to about 82 grams per liter of quantifier and about 0.7 to about 1.1 grams per liter of pH sensitive dye.

13. The device according to claim 1 wherein the wick means has been impregnated from a solution comprising about 120 to about 155 grams per liter of ethylene oxide responsive chemical compound, about 58 to about 78 grams per liter of quantifier and about 0.8 to about 1.0 grams per liter of pH sensitive dye.

14. The device according to claim 1 wherein the perforation has a diameter of about 0.5 to about 0.9 mm.

15. The device according to claim 1 wherein the wick means dimensions are about 1 inch by four inches.

16. The device according to claim 1 wherein the perforation passes through the cover strip as well as the backing strip, and the perforation in the backing strip is sealed by a second ethylene oxide impervious layer.

17. The device according to claim 1 wherein the perforation has a diameter of about 0.4 to about 1.2 mm.

18. The device according to claim 1 wherein the perforation has a diameter of about 0.4 to about 1.2 mm.

19. The device according to claim 1 wherein the wick means is of a dimension of about 3 inches by ¾ inches to about one inch by 4 inches.

* * * * *